United States Patent [19]

Schroeder

[11] Patent Number: 4,637,384
[45] Date of Patent: Jan. 20, 1987

[54] COAXIAL BREATHING CIRCUIT

[75] Inventor: Gerhardt P. Schroeder, Madison, Wis.

[73] Assignee: The BOC Group, Inc., Montvale, N.J.

[21] Appl. No.: 702,561

[22] Filed: Feb. 15, 1985

[51] Int. Cl.$^4$ ............................................. A61M 16/00
[52] U.S. Cl. ................................ 128/204.18; 128/911; 128/912
[58] Field of Search ................... 128/911, 912, 200.14, 128/200.24, 204.18, 205.12

[56] References Cited

U.S. PATENT DOCUMENTS

| | | | |
|---|---|---|---|
| 4,446,863 | 5/1984 | Rubin et al. | 128/204.18 |
| 4,463,755 | 8/1984 | Suzuki | 128/911 |
| 4,521,038 | 6/1985 | Cerny | 128/911 |

Primary Examiner—Henry J. Recla
Attorney, Agent, or Firm—Marshall, O'Toole, Gerstein, Murray & Bicknell

[57] ABSTRACT

A coaxial breathing circuit is disclosed and which includes an inner tube for supplying fresh gas to a patient, which may contain a vaporized anesthetic for anesthetizing the patient, and a corrugated outer tube for conducting the patient's exhaled gases from the patient. At the patient end, there is allowed a slippage between the inner and outer tubes to provide flexibility of the overall circuit to bending. At the the machine end, the end that is connected to a mahcine supplying the inspiratory gas, a connector provides the means to join the inner and outer tubes to a male coupling or directly to a male fitting on the machine. The corrugated outer tube is joined to the connector and an outlet is provided for the discharge of the exhaled gases. For the coaxial circuit to be operable, the inner tube is sandwiched between the outer diameter of the male coupling and the inner diameter of an opening in the connector. In such way, in the event the inner tube becomes disconnected from the male coupling, the entire connector no longer can maintain its connection to the machine and the coaxial circuit drops off completely, thus the possibility of an inadvertent disconnection from the supply of fresh gas is immediately noticeable by attending personnel.

5 Claims, 4 Drawing Figures

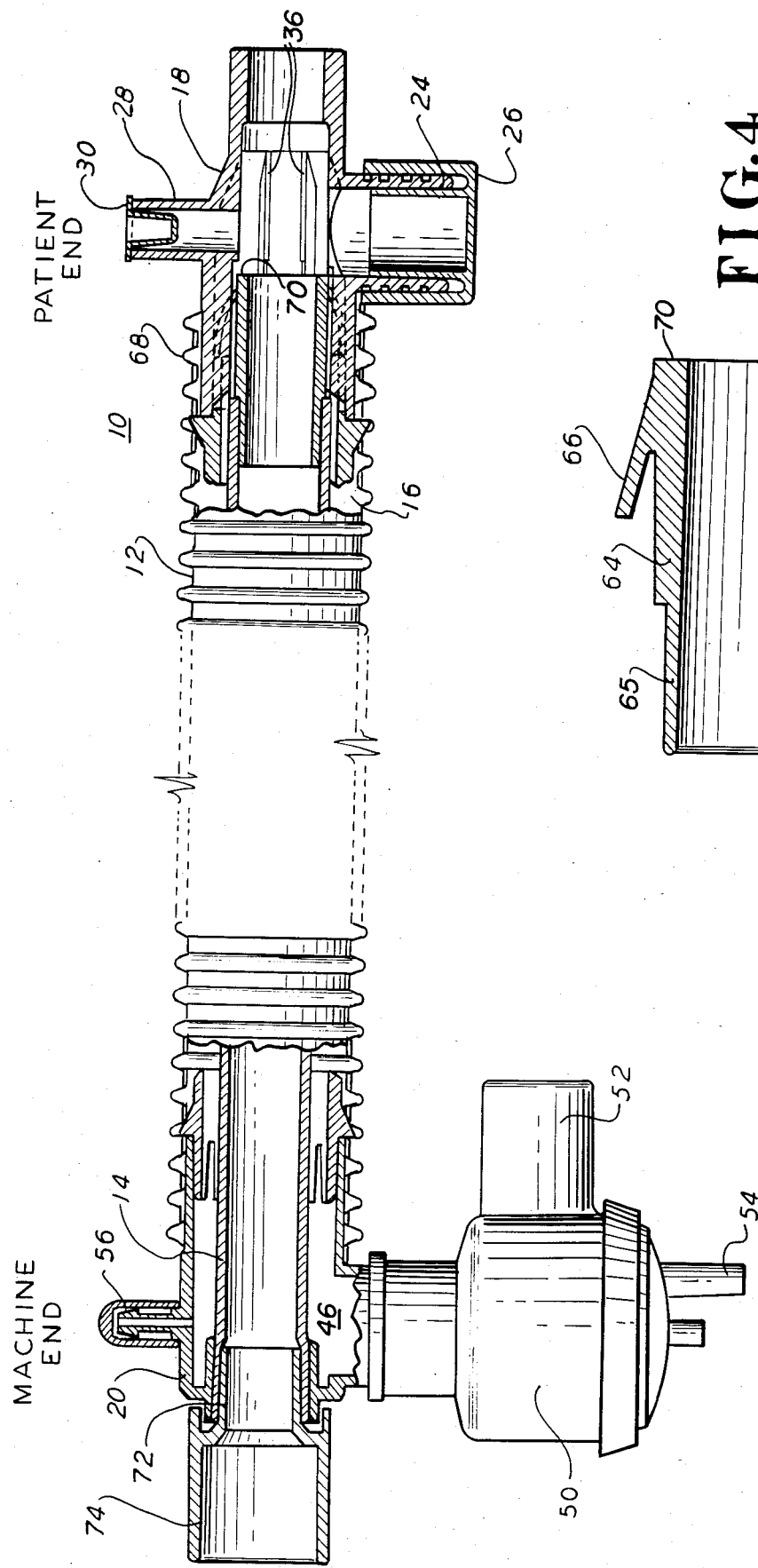
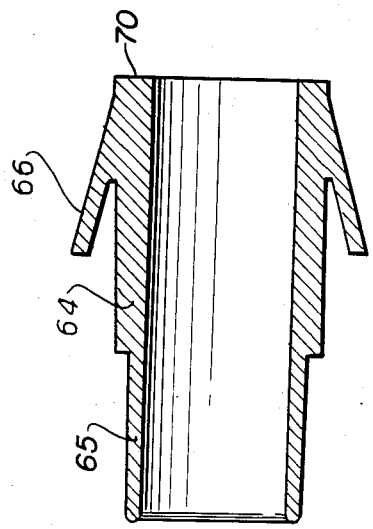

COAXIAL BREATHING CIRCUIT

BACKGROUND OF THE INVENTION

This invention relates generally to a coaxial type of breathing circuit used to supply gas for inhalation by a patient and for receiving and carrying away the patient's exhalation.

Coaxial circuits for breathing circuits have been used for some time, i.e. Bain U.S. Pat. No. 3,856,051, and they include an inner tube that supplies the inhalation gas to the patient. That gas may be air with mixture of $O_2$ in the case of a patient being breathed by a ventilator, or the inhalation gas may include a vaporized anesthetic in the case where a patient is anesthetized.

An outer tube surrounds the inner tube and is generally coaxial therewith. The outer tube is connected to the patient such that a flow path for exhaled gases is formed between the annular space between the inner and outer tubes. The outer tube is generally corrugated for flexibility.

One difficulty with the coaxial circuit, particularly in anesthesia breathing circuits, is the assurance of the integrity of the inhalation circuit. Since the inner tube carries fresh gas to the patient or, in the case of an anesthesia circuit, the anesthetic with fresh gas, it is extremely important for the attending personnel to be immediately aware of an inadvertent disconnection.

At the machine end, a disconnection of the inner tube can escape immediate attention, since its view is shielded by the surrounding corrugated outer tube. Thus, it is possible for the inner tube to be disconnected, yet the overall coaxial circuit has the appearance of being completely intact. The potentially dangerous situation of rebreathing exhaled gases is created, which can result in hypoxia and $CO_2$ buildup in the patient.

SUMMARY OF THE INVENTION

The present invention provides a coaxial breathing circuit wherein a feature is to give a positive and immediate indication of any inadvertent disconnect of the tube providing inhalation gases to the patient.

The coaxial patient circuit includes an inner tube that provides inhalation gases to the patient and an outer, normally corrugated tube that forms, with the inner tube, an annular passageway for carrying away the patient's exhalation. At the patient end, there is a connector that allows both the inner and outer tubes to open into a common chamber, yet that connector also allows a certain amount of slippage between the inner and outer tubes to allow flexibility to the circuit.

At the machine end, another connector interfits the inner and outer tubes, yet maintains separate, the flow passages of each tube. An outlet in the connector allows discharge of the exhalation gases from the annular passageway and a further opening holds the inner tubing sandwiched between a male connector, as would be on a gas machine, or even a further coupling that in turn fits to the machine.

Therefore, the integrity of the connector to the gas machine requires the inner tube to be in place; its inner diameter fits over the male connector, and the connector carrying the outer tube has an opening that is forced over the inner tube, thereby creating the sandwich. In the event the inner tube slips off of the machine, the entire connector will fall of the machine since it no longer can rely upon the inner tube for its forced fit.

Accordingly, even though the connector of the inner tube to the gas machine may not be readily visible to personnel, it will be apparent when the connector is broken; the entire patient circuit will disconnect, thereby alerting personnel to the problem and which can be immediately rectified.

BRIEF DESCRIPTION OF THE DRAWINGS

FIG. 1 is a side view, partly in cross-section and broken away, showing the coaxial patient circuit of the present invention; FIG. 4 is a slip fit connector used with the present circuit.

DESCRIPTION OF PREFERRED EMBODIMENT

Figure 2:
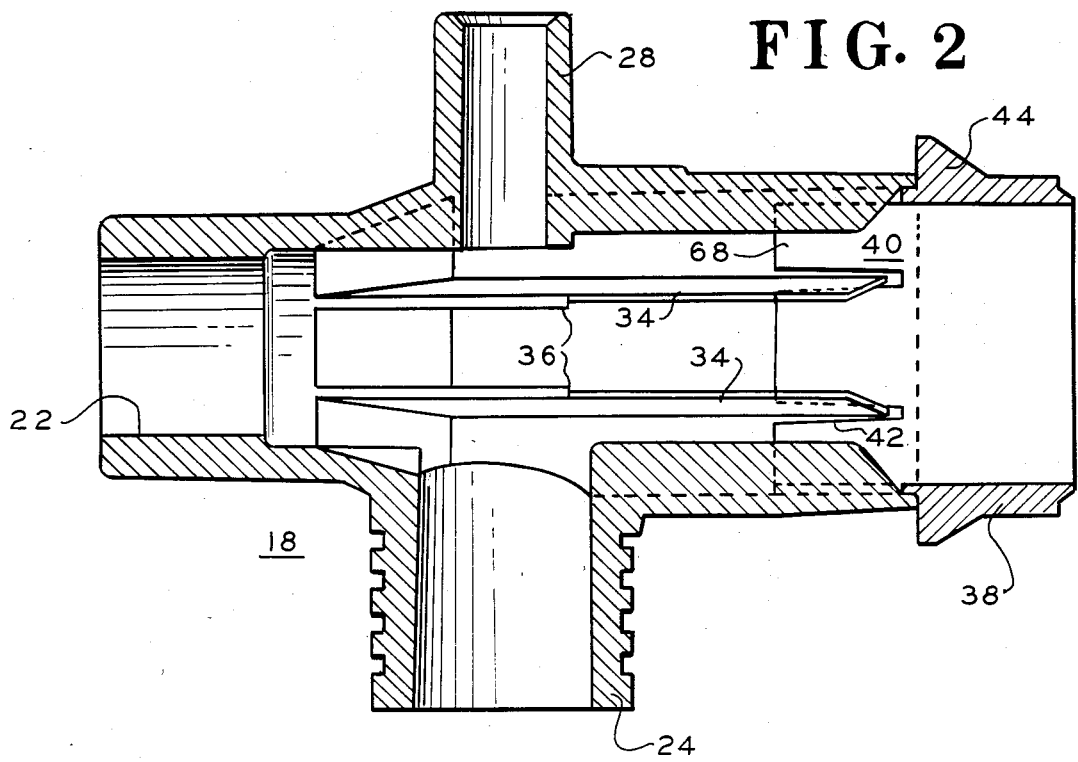
FIG. 2 is a side cross-sectional view of the patient end connector used with the circuit of FIG. 1.

Referring now to FIG. 1, there is shown a coaxial patient circuit 10 having, as labeled, a patient end and a machine end. As will be described, the patient end is that end of the circuit to be attached to a patient administration device, such as a face mask to provide the gas to and from the patient. The machine end of the circuit is that end which is attached to a gas machine that provides the gas to the patient and which breathes for the patient by cyclically pressurizing the supply of gas. That machine may, of course, be a respirator which supplies air, or oxygen enriched air to the patient, or includes an anesthesia ventilator where, in addition to life-supporting gas mixture, there is added a vaporized anesthetic, such as enflurane or isoflurane to anesthetize the patient.

The coaxial patient circuit 10 generally comprises an outer tube 12 and an inner tube 14. The inner tube 14 carries gases to the patient for inhalation and is generally of stabilized polyvinyl chloride material so as to allow flexibility. The outer tube 12 may also be of a flexible material and is preferably corrugated for strength and flexibility. An annular passageway 16 is thus formed between the generally coaxial outer tube 12 and inner tube 14 and carries the patient's exhaled gases as will later be explained.

A patient end connector 18 and a machine end connector 20 are provided for joining the tubes 12 and 14 to their respective devices and for channeling the inhalation and exhalation gases as desired.

Taking first the patient end connector 18, and which is more clearly shown in FIG. 2, there is an opening 22 which is sized to form an interference fit with a patient administration device, such as a mask having a male connector. A further port 24 may conventionally be available for other devices and, as shown, is covered by a cap 26 (FIG. 1 only).

A further sampling port 28 can also be utilized for monitoring the pressure in the coaxial patient circuit 10 since, as a feature of this type of circuit, the pressure at the patient end is basically the same pressure throughout the circuit. Again, a cap 30 seals the sampling port 28 in the event it is not used (only shown in FIG. 1).

Inside the patient end connector 18 is a chamber 32 where inhalation and exhalation gases are delivered to, and received from, respectively, the opening 22. A plurality of inwardly directed fins 34 are formed on the internal surface of patient end connector 20 and serve to guide the inner tube 14 as will be later explained. Also the fins 34 have shoulders 36 that form an opening of smaller diameter than the fins 34 and stop the movement, in one direction, of the inner tube 14 within the patient end connector 18.

A barb connector 38 fits against the patient end connector 18 and includes a flange 40 that enters the connector 18 and is sealed thereagainst by means such as solvent bonding. A plurality of slots 42 interfit with fins 34.

The barb connector 38 has on its outer periphery an annular barb 44 that is shaped such as to allow the outer tube 12 to be slipped on to the patient end connector, yet resist its removal therefrom.

Figure 3:
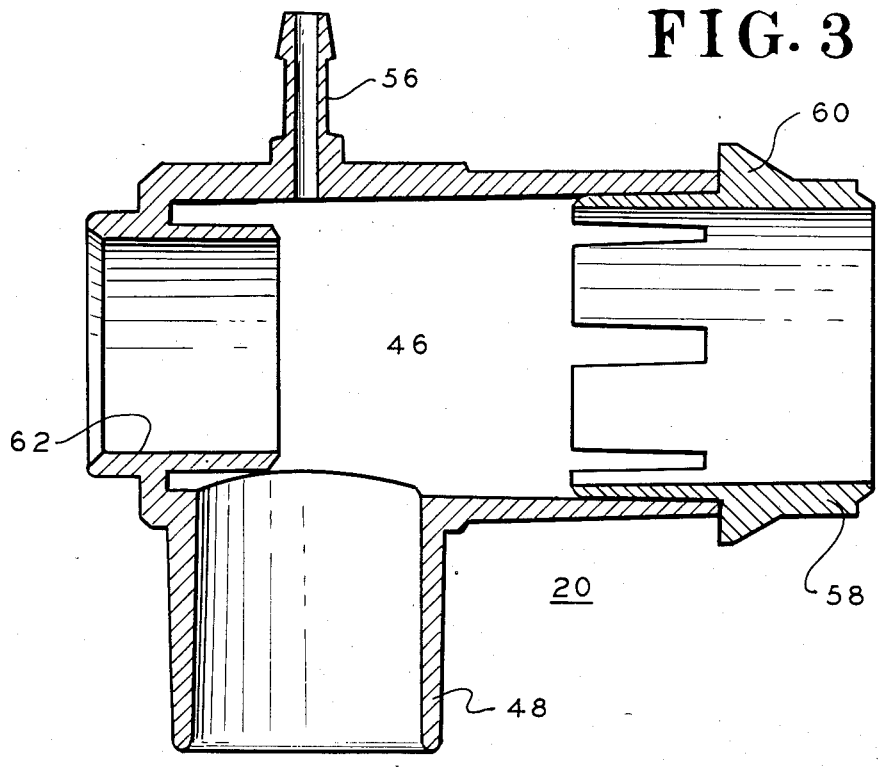
FIG. 3 is a side cross-sectional view of the machine end connector used with the circuit of FIG. 1.

Turning now to the machine end connector 20, as shown in FIG. 1 and FIG. 3, the connector 20 is of molded polypropylene or TPX material having an internal chamber 46 and including an outlet 48 for discharge of the patient's exhaled gases. With respect to FIG. 1 only, that flow of exhaled gas may be controlled by conventional exhalation valve 50 of the diaphragm type, including a discharge outlet 52 and a control port 54 for controlling the force on one side of the diaphragm, and may be used to establish a positive end expiratory pressure (PEEP) for the circuit. Again, a pressure port 56 may be included to monitor the pressure within the circuit 10.

A barb connector 58 is fitted into the end of the machine end connector 20 that faces away from the machine and, again, similar to barb connector 38, may be affixed thereto by means such as solvent bonding. The barb connector also has a barb 60 surrounding its periphery for retaining the outer tube 12 in position connected to the machine end connector 20.

A machine end connector 20 also includes an inlet opening 62 which combines by utilizing the thickness of the inner tube 14 for connecting the coaxial patient circuit 10 to the gas machine.

A final port used for assembling the coaxial breathing circuit 10 is shown in FIG. 4 as an inner tube end piece 64. The end piece 64 has a cylindrical flange 66 that fits within and is thus secured to the inner tube 14. At its other end, there are formed a plurality of tabs 66 that are molded with the end piece 64 and which depend outwardly at an angle. Because of the type of material used to mold end piece 64, the tabs 66 can be flexed inwardly and, when released, return to their outward position as shown in FIG. 4.

The assembly of the coaxial patient circuit can now be described as follows, referring specifically to FIG. 1. The end of the inner tube 14 having affixed thereto, the end piece 64 is inserted into the end of the patient end connector 18 on which the barb connector 38 is attached. As the end piece 64 is inserted, its tabs 66 are compressed and, when the tabs 66 move past the innermost end 68, tabs 66 spring outward and prevent the end piece 64 from being withdrawn from patient end connector 18. End piece 64 can slide to a certain extent within patient end connector 18 having its forward travel stopped by abutting the front surface 70 of end piece 64 against shoulders 36 of fins 34. Movement in the withdrawing direction is, of course, stopped by tabs 66 abutting against the end 68 of barb connector 38. Thus the end piece can freely slide within patient end connector within certain predetermined limits.

The outer tube 12 is easily assembled to the patient end connector 18 by being slid over the barb connector 38 sufficient distance that the barb 44 fits within one of the corrugations and prevents removal of the outer tube 12 from patient end connector 18.

At the machine end of the coaxial patient circuit 10, the inner tube 14 can be slid over a male connector 72. As shown, the male connector 72 is a part of a separate fitting 74 that, in turn, has an opening 76 that interfits with a gas machine. In this way, the coaxial patient circuit 10 can be sold already assembled; however, it may be seen that the male connector 72 may be a part of the gas machine itself.

In either event, the machine end connector 20 is joined to the male connector 72 by first forcing the machine end of inner tube 14 over the male connector 72. The inlet opening 62 of the machine end connector 20 is then forced over the external surface of inner tube 14, thereby sandwiching the inner tube 14 between the male connector 72 and the inlet opening 62. As long as that force fit sandwich persists, the machine end connector 20 will be retained on the male connector 72. If, however, at any time, the inner tube 14 becomes disconnected from male connector 72, the inlet opening 62 will be too large to fit onto the male connector 72 and the machine connector 20 as well as the entire coaxial patient circuit 10 will fall from the gas machine, thus making it obvious to attending personnel that the inner tube 14 has become disengaged.

The final assembly step is again to slip the corrugated outer tube 12 over the barb 60 of barb connector 58, thus holding it in place on the machine end connector 20.

Thus, it may also be seen that the inhalation gases from the machine follow a separate flow path through the machine end connector 20 by passing directly into and through the inner tube 14. The exhaled gases from the patient flow through annular passageway 16 into the internal chamber 46 of machine end connector 20 and thereafter separately out the outlet 48 and through exhalation valve 50.

While the present invention has been particularly set forth in terms of specific embodiments thereof, it will be understood in view of the instant disclosure that numerous variations upon the invention are now enabled to those skilled in the art, which variations yet reside within the scope of the instant teaching. Accordingly, the invention is to be broadly construed and limited only by the scope and spirit of the claim now appended hereto.

I claim:
1. A patient breathing circuit for providing gases from a breathing machine to a patient comprising:
   a flexible corrugated outer tubing;
   a flexible inner tubing generally coaxial with said outer tubing forming a first gas path between said inner and outer tubings, and a second gas path within said inner tubing;
   a patient end connector attached to one end of said outer tubing and said inner tubing and forming a path between said first and second gas paths to the patient, said patient end connector comprising a tube end piece having one end secured to said one end of said inner tubing, said end piece including a flexible tab portion which angles radially outwardly and in the direction of said inner tubing, said patient end connector further comprising housing means forming a cylindrical flow chamber, at least three ribs radially spaced around the inside surface of said cylindrical flow chamber and extending longitudinally of and, generally radially into said chamber, and first and second longitudinally spaced apart stop means in said chamber, said tube end piece being slidably positioned along said ribs within said chamber and spaced therefrom by said ribs, and said tube end piece having an opposite end being engaged with said first stop means to allow limited sliding movement of said end piece within said housing in one direction and said flexible tab portion being engaged with said second stop means to allow limited sliding movement of said end piece within said housing in an opposite direction; and a machine end connector connected to the other ends of said inner and outer tubings, said machine end connector having an outlet for discharging gas from said first gas path, said machine end connector further having an opening of predetermined internal diameter through which said inner tubing at least partially extends; a male connector to provide gas to said second gas path from said machine, said male connector having a portion of predetermined external diameter, said portion being within said inner tubing and extending through said opening to frictionally engage and sandwich said inner tubing between said portion and said opening; said inner tubing thereby being affixed to said male connector solely by means of the engagement through said inner tubing.

2. A patient breathing circuit as defined in claim 1 wherein said opening in said machine end connector is in axial alignment with said inner tubing.

3. A patient breathing circuit for providing gases from a breathing machine to a patient comprising:
a flexible corrugated outer tubing;
a flexible inner tubing generally coaxial with said outer tubing forming a first gas path between said inner and outer tubings, and a second gas path within said inner tubing; a machine end connector secured to one end of said inner and outer tubings and forming separate flow passages connected respectively to said first and second gas paths; and a patient end connector attached to the other end of said inner and outer tubings and forming a path between said first and second gas paths to the patient, said patient end connector comprising a tube end piece having one end secured to said other end of said inner tubing, said end piece including a flexible tab portion which angles radially outwardly and in the direction of said inner tubing, said patient end connector further comprising housing means forming a cylindrical flow chamber, at least three ribs radially spaced around the inside surface of said cylindrical flow chamber and extending longitudinally of and generally radially into said chamber, and first and second longitudinally spaced apart stop means in said chamber, said tube end piece being slidably positioned along said ribs within said chamber and spaced therefrom by said ribs, and said tube end piece having an opposite end being engaged with said first stop means to allow limited sliding movement of said end piece within said housing in one direction and said flexible tab portion being engaged with said second stop means to allow limited sliding movement of said end piece within said housing in an opposite direction.

4. Apparatus set out in claim 3, wherein said first gas path extends between said ribs and said tube end piece.

5. Apparatus as set out in claim 3, wherein said stop surfaces are formed by end surfaces of said tab portion and said opposite end of said tube end piece, and said first and second stop means are formed by shoulders on said inside surface of said housing and on said ribs, said shoulders being spaced a greater distance than the spacing between said end surfaces to enable said end piece to slide in said housing.

* * * * *